United States Patent
Egilsson

(10) Patent No.: US 8,097,043 B2
(45) Date of Patent: Jan. 17, 2012

(54) SUSPENSION LINER WITH SEAL

(75) Inventor: Egill Sveinbjorn Egilsson, Reykjavik (IS)

(73) Assignee: Ossur HF, Reykjavik (IS)

( * ) Notice: Subject to any disclaimer, the term of this patent is extended or adjusted under 35 U.S.C. 154(b) by 0 days.

(21) Appl. No.: 12/818,426

(22) Filed: Jun. 18, 2010

(65) Prior Publication Data

US 2010/0318196 A1    Dec. 16, 2010

Related U.S. Application Data

(60) Continuation of application No. 11/135,354, filed on May 24, 2005, now Pat. No. 7,749,281, which is a division of application No. 10/690,545, filed on Oct. 23, 2003, now Pat. No. 7,025,793.

(60) Provisional application No. 60/434,669, filed on Dec. 20, 2002.

(51) Int. Cl.
*A61F 2/78* (2006.01)

(52) U.S. Cl. .......................................................... 623/34

(58) Field of Classification Search .............. 623/32–37; 602/62–63
See application file for complete search history.

(56) References Cited

U.S. PATENT DOCUMENTS

| | | |
|---|---|---|
| 980,457 A | 1/1911 | Toles |
| 1,398,824 A | 11/1921 | Abrams |
| 1,893,853 A | 12/1931 | Tullis |
| 2,530,285 A | 11/1950 | Catranis |
| 2,533,404 A | 12/1950 | Sharp et al. |
| 2,634,424 A | 4/1953 | O'Gorman |
| 2,671,225 A | 3/1954 | Schoene et al. |
| 2,808,593 A | 10/1957 | Andersen |
| 3,393,407 A | 7/1968 | Kandel |
| 3,671,980 A | 6/1972 | Baird |
| 4,923,474 A | 5/1990 | Klasson et al. |
| 5,007,937 A | 4/1991 | Fishman et al. ................. 623/34 |
| 5,139,523 A | 8/1992 | Paton et al. ..................... 623/37 |
| 5,163,965 A | 11/1992 | Rasmusson et al. ............ 623/36 |
| 5,226,918 A | 7/1993 | Silagy et al. .................... 623/32 |
| 5,314,496 A | 5/1994 | Harris et al. |
| 5,376,129 A | 12/1994 | Faulkner et al. ................ 623/33 |
| 5,376,131 A | 12/1994 | Lenze et al. |
| 5,549,709 A | 8/1996 | Caspers |
| 5,658,353 A | 8/1997 | Layton |
| 5,702,489 A | 12/1997 | Slemker ......................... 623/34 |
| 5,718,925 A | 2/1998 | Kristinsson et al. ............. 425/2 |
| 5,728,170 A | 3/1998 | Becker et al. ................... 623/37 |

(Continued)

FOREIGN PATENT DOCUMENTS

DE    745 981    12/1943

(Continued)

OTHER PUBLICATIONS

EP 03 78 9861—Supplementary European Search Report, Oct. 5, 2009; 2 pages.

*Primary Examiner* — David H. Willse
(74) *Attorney, Agent, or Firm* — Bacon & Thomas, PLLC

(57) ABSTRACT

A suspension liner sleeve providing an interface between a residual limb and a hard prosthetic socket includes a resilient seal element extending around its outer periphery to enhance a sealing effect between the sleeve and the interior of a prosthetic socket to isolate the distal end of the socket from atmosphere after the sleeve with a residual limb has been inserted within the socket and to thereby improve the retention of the liner sleeve and the residual limb in the prosthetic socket.

19 Claims, 7 Drawing Sheets

U.S. PATENT DOCUMENTS

| | | |
|---|---|---|
| 5,735,906 A | 4/1998 | Caspers |
| 5,888,216 A | 3/1999 | Haberman |
| 5,904,722 A | 5/1999 | Caspers |
| 5,931,872 A | 8/1999 | Lohmann ................. 623/36 |
| 5,972,036 A | 10/1999 | Kristinsson et al. ........... 623/33 |
| 6,149,691 A | 11/2000 | Fay et al. ................. 623/37 |
| 6,231,616 B1 | 5/2001 | Helmy ................. 623/34 |
| 6,231,617 B1 | 5/2001 | Fay |
| 6,273,918 B1 | 8/2001 | Yuhasz et al. ............ 623/33 |
| 6,287,345 B1 | 9/2001 | Slemker et al. ........... 623/34 |
| 6,361,568 B1 | 3/2002 | Hoerner ................. 623/32 |
| 6,508,842 B1 | 1/2003 | Caspers |
| 6,554,868 B1 | 4/2003 | Caspers |
| 6,585,774 B2 | 7/2003 | Dean, Jr. et al. ........... 623/37 |
| 6,645,253 B2 | 11/2003 | Caspers |
| 6,726,726 B2 | 4/2004 | Caspers |
| 6,761,742 B2 | 7/2004 | Caspers |
| 7,144,429 B2 | 12/2006 | Carstens |
| 2001/0005798 A1 | 6/2001 | Caspers |
| 2001/0016781 A1 | 8/2001 | Caspers |
| 2002/0040248 A1 | 4/2002 | Karason ................. 623/37 |
| 2002/0087215 A1 | 7/2002 | Caspers ................. 623/34 |
| 2002/0091449 A1 | 7/2002 | Caspers et al. |
| 2002/0099450 A1 | 7/2002 | Dean, Jr. et al. ........... 623/26 |
| 2003/0191539 A1 | 10/2003 | Caspers |
| 2004/0030411 A1 | 2/2004 | Caspers |
| 2004/0098136 A1 | 5/2004 | Caspers |
| 2004/0122528 A1 | 6/2004 | Egilsson |
| 2004/0143345 A1 | 7/2004 | Caspers |
| 2004/0167638 A1 | 8/2004 | Caspers ................. 623/27 |
| 2004/0181290 A1 | 9/2004 | Caspers |
| 2004/0236434 A1 | 11/2004 | Carstens ................. 623/34 |
| 2004/0243251 A1 | 12/2004 | Carstens ................. 623/34 |
| 2004/0243252 A1 | 12/2004 | Carstens ................. 623/34 |

FOREIGN PATENT DOCUMENTS

| | | |
|---|---|---|
| DE | 813190 | 7/1951 |
| DE | 1795809 | 9/1959 |
| DE | 2060239 | 6/1972 |
| DE | 2540138 | 3/1977 |
| DE | 3221920 | 6/1982 |
| DE | 3221920 | 4/1983 |
| DE | 3508919 | 9/1986 |
| DE | 9419208.1 | 11/1994 |
| EP | 631765 | 4/1995 |
| GB | 267988 | 3/1927 |
| GB | 2 069 847 | 9/1981 |
| GB | 2 087 727 | 6/1982 |
| JP | 7155343 | 6/1995 |
| WO | 00/74611 A2 | 12/2000 |
| WO | 01/54631 A1 | 8/2001 |
| WO | WO 01/54631 | 8/2001 |
| WO | 03/024367 | 3/2003 |
| WO | 03/024370 | 3/2003 |
| WO | 03/039398 | 5/2003 |
| WO | 03/099173 A1 | 12/2003 |

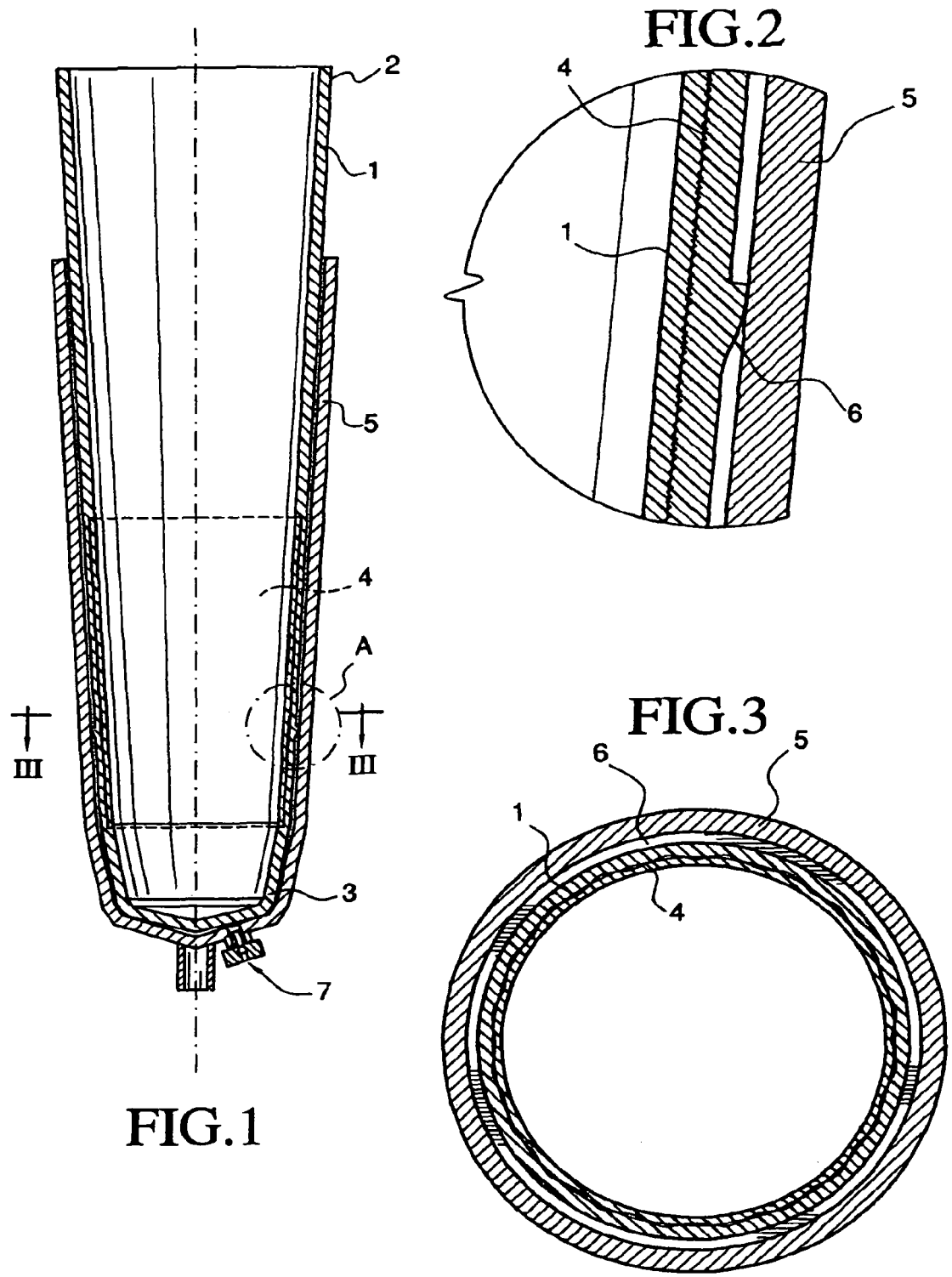

 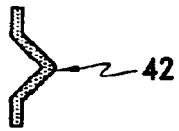 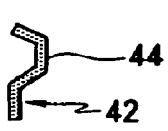 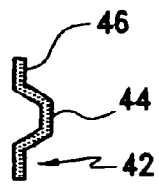
FIG. 21   FIG. 22   FIG. 23   FIG. 24
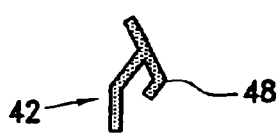 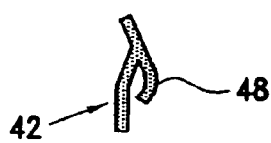 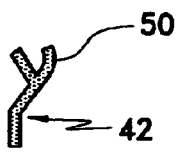 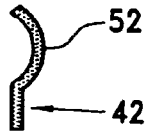
FIG. 25   FIG. 26   FIG. 27   FIG. 28
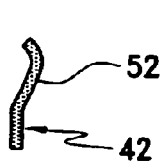 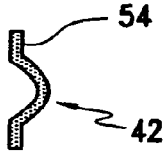 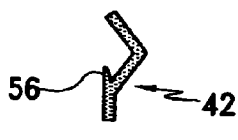 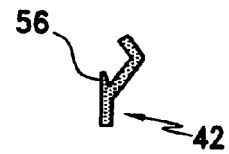
FIG. 29   FIG. 30   FIG. 31   FIG. 32
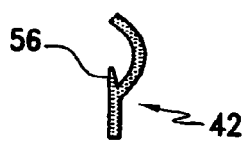 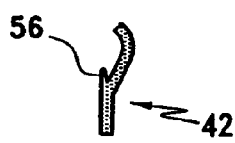 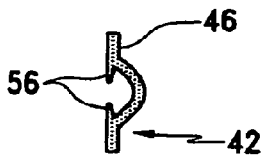
FIG. 33   FIG. 34   FIG. 35

SUSPENSION LINER WITH SEAL

CROSS REFERENCE TO RELATED APPLICATION

This application is a continuation application of U.S. patent application Ser. No. 11/135,354, filed May 24, 2005, issued as U.S. Pat. No. 7,749,281 on Jul. 6, 2010, which is a divisional application of U.S. patent application Ser. No. 10/690,545 filed Oct. 23, 2003, issued as U.S. Pat. No. 7,025,793 on Apr. 11, 2006, and further claims the benefit of the filing date under 35 U.S.C. §1.19(e) of U.S. provisional application Ser. No. 60/434,669, filed Dec. 20, 2002, the contents of all of which are incorporated by reference herein in their entirety.

BACKGROUND OF THE INVENTION a. Field of the Invention

This invention relates to suspension liner sleeves adapted to provide an interface between a residual limb and a prosthetic socket.

b. Discussion of Related Art

Suspension liner sleeves adapted to provide a soft, flexible interface between a residual limb of an amputee and a hard socket to which a prosthetic device is secured is known in the art generally, as exemplified by U.S. Pat. No. 4,923,474 granted May 8, 1990 to Klasson and Kristinsson. Such liner sleeves are typically made of an air impermeable elastomer material such as silicone and may include a reinforcement layer intermediate the inner and outer surfaces of the liner sleeve body portion or externally thereof to provide resistance against axial elongation of the elastomer constituting the liner sleeve body. Such reinforcement typically does not restrict radial distension or stretching of the liner sleeve body.

In accordance with prior art teachings, such liner sleeves, sometimes called suspension sleeves, may function to secure the residual limb within the prosthetic socket member once the residual limb and sleeve are inserted into the socket in close-fitting relationship by isolating the distal end area of the hard socket from the atmosphere. Upon application of a pulling force on the liner sleeve relative to the socket, a suction is created in the distal end of the socket tending to retain the liner sleeve within the socket. Appropriate devices are usually provided to enable expulsion of air between the distal end of the liner sleeve and the hard socket and to isolate the distal end of the hard socket member from the atmosphere after the liner sleeve with a residual limb has been fully inserted within the socket member.

In some applications, the liner sleeve is provided with an "umbrella" at its distal end and a threaded socket for receiving a prosthetic securing pin member which then extends through an axial opening in the distal end of the hard socket member for securing the socket member relative to a prosthetic device mounted to the distal end of the socket member.

In other applications, the prosthetic device is secured to the exterior of the distal end of the hard socket member and the sleeve member is fully contained within the hard socket member.

The elastomer constituting the liner sleeve member frictionally engages and remains attached to the skin of a residual limb so that the limb is retained within the hard socket member in a comfortable, non-irritating manner. The liner sleeve may be thickened to provide cushioning effect between the residual limb and the hard socket, which is typically custom made to closely fit the residual limb. Liner sleeves of this kind are used for both trans-tibial (TT) amputees as well as trans-femoral (TF) amputees. That is, the liner sleeves may be utilized for applications above the knee or below the knee of the amputee.

In other applications, it may be desired to more positively secure the liner sleeve within the socket by creating a hypobaric (vacuum) pressure within the distal end of the hard socket between such distal end and the distal end of a liner sleeve inserted into the socket with a residual limb contained within the liner sleeve. The hypobaric pressure may be maintained at the distal end of the hard socket and the interior of the socket at its distal end will be isolated from atmosphere during normal retention of the sleeve liner within the socket. Opening the distal end of the socket to atmosphere releases the vacuum or hypobaric pressure within the socket to enable simple withdrawal of a residual limb with a liner sleeve thereon from the socket.

A pump or other device may be utilized to evacuate the distal end of the socket between the distal end of a liner sleeve and the distal end of a socket. A valve or other appropriate device typically is used to open and close the distal end of a socket to surrounding atmosphere.

Various arrangements are known in the prior art for providing an appropriate seal between the exterior of the liner sleeve and the interior of the hard socket including external air impermeable sleeves covering the interface area between the proximal end of the hard socket and the adjacent liner sleeve body.

In trans-femoral applications, the sealing between a liner sleeve and a socket is generally simpler and easier to execute than sealing a trans-tibial liner sleeve against the inner surface of a socket because in the latter situation, the residual limb contains more bony protuberances and irregular shapes that are difficult to effectively seal, particularly if it is desired to simply use the material of the elastomeric liner sleeve as the sealing element.

It is an objective of this invention to create a convenient, improved sealing arrangement between an elastomeric liner sleeve and the interior of a prosthetic socket having advantages for trans-tibial liner sleeves.

BRIEF SUMMARY OF THE INVENTION

In accordance with the present invention, an elastomeric liner sleeve having an elongate, generally conical, air impermeable body portion that is typically freely radially elastically distensible from a relaxed non-extended condition and including proximal and distal end areas is provided with a resilient seal element protruding radially from a liner sleeve body portion between its proximal and distal end areas, such resilient seal element extending around an entire peripheral portion of the liner sleeve body portion.

In one embodiment, the resilient seal element may be integrally formed in one piece with the liner sleeve body portion and is located closer to its distal end than its proximal end. Alternatively, the seal also may be formed separately from the liner sleeve body portion, and it may be constituted of an assembly of elements or an element that is securely attached to the exterior of the liner sleeve body portion. The seal may be located at appropriate other locations along the liner sleeve length, and may include multiple sealing surfaces.

The liner sleeve may include a reinforcement material associated with the liner sleeve body portion that extends over a length that coincides at least with the location of the resilient seal element and which extends longitudinally along the liner sleeve body portion in the area of the seal element, including above and below the seal element. The reinforcement material is designed to provide greater elastic stiffness along the axial direction of the liner sleeve body portion as compared with the radial direction thereof. The reinforcement material thus serves to distribute tension loads imposed on the distal end area of the liner sleeve body portion over the axial length thereof where the reinforcement material is provided.

The liner sleeve may include a recessed portion extending continuously around a peripheral portion of the liner sleeve body portion whereat the seal element may be secured. The recessed portion is configured to accommodate compression of the seal element. The reinforcement material in this embodiment may be positioned above or at the seal element and extend substantially towards and around a distal end area of the liner sleeve so as to reinforce the distal end area of the liner sleeve.

In use, a residual limb is placed within the liner sleeve body portion according to the invention and both the residual limb and the liner sleeve body portion are inserted within a hard socket of a prosthetic system so that the peripheral seal element engages an inner wall of the hard socket to isolate the distal end area of the hard socket from surrounding atmosphere. Creation of a hypobaric pressure within the distal end area of the hard socket or simple evacuation or venting of air between the distal end area of the liner sleeve body portion and the distal end of the hard socket followed by sealing off the area between the liner sleeve body portion and the internal distal end of the socket serves to effectively retain the liner sleeve within the socket of the prosthetic system, with the seal effectively isolating the distal end of the hard socket externally of the liner sleeve from atmosphere.

Whether a hypobaric pressure is created within the distal end area of the hard socket or if the distal end is merely isolated from atmosphere, withdrawal of the liner sleeve body portion and the residual limb contained therein will be resisted strongly by the creation of or maintenance of a suction between the distal end of the liner sleeve body portion and the interior distal end area of the hard socket when a pulling force tending to extricate the liner sleeve body portion from the prosthetic socket is applied.

The suction may be released between the hard socket and the liner sleeve simply by exposing the interior distal end area of the hard socket to atmosphere.

The seal element serves to provide a positive sealing effect by its resilient compression between the inner wall of the hard socket and the liner sleeve body portion due to the radial force of the residual limb within the liner sleeve body portion. The peripherally extending seal takes up irregularities between the exterior of the liner sleeve and the interior of the socket irrespective of bony protuberances, irregularities and non-cylindrical forms of the residual limb. Because the socket is already configured to closely approximate the exterior shape of the residual limb, the seal simply follows the contour of the inner surface of the socket to isolate the distal end of the socket from atmosphere when the liner sleeve is inserted into the socket.

BRIEF DESCRIPTION OF THE DRAWINGS

With reference to the appended drawings,

FIG. 1 is a vertical sectional view of a prosthesis system including a hard socket, an elastomer liner sleeve having a reinforcement material embedded in the liner sleeve body portion and further including a peripheral seal element integrated with the elastomer liner sleeve;

FIG. 2 is a detail corresponding to detail A in FIG. 1; and

FIG. 3 is a sectional view taken along line III-III in FIG. 1.

FIGS. 21-35 are vertical sectional views of alternate forms of the peripheral seal element illustrated in FIG. 17.

DETAILED DESCRIPTION OF PREFERRED EMBODIMENT OF THE INVENTION

Figure 4:
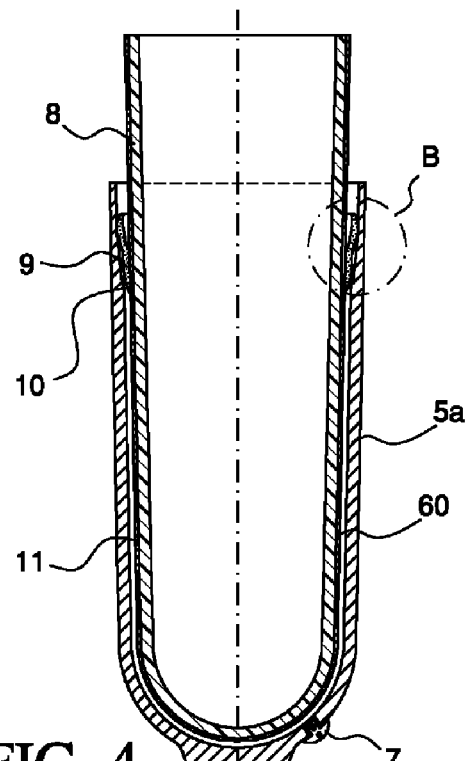
FIGS. 4-10 are vertical sectional views of a prosthesis system corresponding to FIG. 1 wherein alternate forms of peripheral seal elements are illustrated.

With reference to FIG. 1, an elastomer liner sleeve body portion 1, for example made of silicone, is formed as an elongate, generally conical member as is well known in the art and as is further described in U.S. Pat. No. 4,923,474, the entirety of which is incorporated herein by reference.

The liner sleeve body portion may be formed of various elastomer materials that are known to those skilled in the art and that are typically used for the manufacture of prosthetic liner sleeves.

The liner sleeve extends between a proximal end 2 and a distal end area 3. The liner sleeve body portion is soft and at least radially distensible elastically. The liner sleeve also may be elastically distensible axially or may have limited axial elasticity or at least a greater elastic stiffness (resistance to distension) in an axial sense as compared with its radial elasticity, but such anisotropy is optional.

If it is desired to increase the axial stiffness of the liner sleeve body portion 1, a reinforcement material 4 is integrated into the elastomer of the liner sleeve body portion, for example in the manner described in U.S. Pat. No. 4,923,474. Various reinforcement materials may be utilized to limit axial distension of the liner sleeve body portion and typically a material that is axially stiff but radially compliant is preferred. Thus, the combination of the elastomer material constituting the liner sleeve body portion and the reinforcement body material results in a liner sleeve that resists elongation in the axial direction in the event that tension is applied to the liner sleeve material while the sleeve is fully radially compliant elastically so as not to unduly compress a residual limb contained within the liner sleeve or restrict its ability to fill the hard socket member. The reinforcement material 4 alternatively may be located externally of the elastomer, such as a textile cover on the elastomer liner sleeve body, for example in FIGS. 4 and 11, and denoted by layer 60.

The liner sleeve 1 is typically donned on a residual limb and the limb and sleeve are then inserted into the prosthetic socket 5 which is typically rigid or hard in order to carry loads transferred from a prosthetic device attached to the socket to the residual limb and vice-versa.

The softer elastomer of the liner sleeve body portion adheres to the skin of a residual limb frictionally to thereby secure the limb within the sleeve. The liner sleeve, on the other hand, remains contained within the hard socket 5 after it has been fully inserted to the distal end area of the hard socket by effectively isolating the interior of the hard socket 5 from atmosphere.

Any pulling forces applied to the liner sleeve will result in a suction being created between the distal end of the liner sleeve and the interior of the hard socket at its distal end area. The increased stiffness in an axial sense created by the reinforcement material minimizes pumping action on the residual limb and creates a stiffer interface between the residual limb and the liner sleeve in the area occupied by the reinforcement material.

In accordance with the embodiment illustrated in FIG. 1, the reinforcement material 4 extends over a limited distal end area of the liner sleeve, but could extend fully around the distal end area of the liner sleeve, if desired, as shown, for example, in U.S. Pat. No. 4,923,474, and up to the proximal end 2 of the liner sleeve.

To further enhance isolation of the distal end area of the hard socket from atmosphere, a seal element 6 associated with the liner sleeve is provided. The seal element 6 could be formed of the same silicone material as the liner sleeve body portion 1 and created integrally in one piece with the liner sleeve body portion 1 during molding or forming of the liner sleeve body portion 1, or, alternatively, could be formed separately of a softer or stiffer material or a material more suitable for a seal than the material forming the liner sleeve body portion, and then secured to the liner sleeve.

The seal element 6 may be tapered outwardly from its distal end towards its proximal end to facilitate insertion of the liner sleeve body portion 1 into the hard socket 5 and tends to resist outward movement of the liner sleeve from the hard socket. Also, the form of seal element 6 preferably provides an increased sealing force between the liner sleeve 1 and the hard socket 5 when the liner sleeve 1 is moved in a direction tending to withdraw it from the hard socket, or in other words, the seal element 6 seals more effectively in a direction towards the liner sleeve distal end when subjected to a pressure differential where a lower pressure exists towards the distal side of the seal as compared to the proximal side thereof.

If desired, the seal element 6 could be formed as a separate element or assembly of elements attached to or otherwise secured to the liner sleeve body portion 1, as will be described below. It will be apparent that any manufacturing technique known to those skilled in the art could be utilized to create an enlarged seal element 6 surrounding the peripheral area of the liner sleeve body portion 1 at an area thereof between the proximal and distal end areas 2, 3 of the liner sleeve body portion 1 so that, upon insertion of the liner sleeve body portion into a hard socket 5, the seal 6 isolates the distal end area of the interior of the hard socket 5 from atmosphere between the seal 6 and the distal end area of the hard socket 5. While a single seal element may be utilized in accordance with the present invention, a plurality of seal rings 6 secured to the liner sleeve could be utilized to provide enhanced sealing effect, as will be described below.

When the liner sleeve body portion 1 is fully inserted into the socket 5, the seal 6 fully isolates the interior of the socket distal end area from atmosphere until communication is provided between the interior of the socket distal end and atmosphere.

To permit purging of air from the distal end of the socket 5 while the liner sleeve body portion 1 and its associated seal 6 are inserted into the socket, an appropriate one way valve element 7 may be provided, or a valve capable of opening and closing manually may be used to isolate the interior of the distal end of the socket 5 from atmosphere.

It will be apparent that, when the liner sleeve body portion 1 is fully inserted into the socket 5 with the seal 6 isolating the distal end area of the socket 5 from atmosphere, all pulling loads tending to withdraw the liner sleeve from the socket will result in a suction being created between the distal end area of the liner sleeve 1 and the distal end of the socket 5. The seal 6 further enhances and maintains the suction between the liner sleeve body portion 1 and the socket 5. The presence of the reinforcement material in the vicinity of the seal 6 further enhances the function of the seal element 6 in maintaining the distal end area of the socket 5 isolated from atmosphere when the residual limb and its associated liner sleeve body portion 1 have been fully inserted into the socket due to better distribution of loads between the socket 5, the liner sleeve body portion, and a residual limb.

If desired, a hypobaric pressure could be created between the distal end area of the liner sleeve body portion 1 and the distal end of the socket 5 by attaching a pump or other device that enables evacuation of atmosphere between the seal 6 and the distal end of the socket 5.

With reference to FIGS. 4-16, various alternative preferred forms of liner sleeve body portions, seal elements and hard socket interior configurations are illustrated by way of example.

Figure 11:
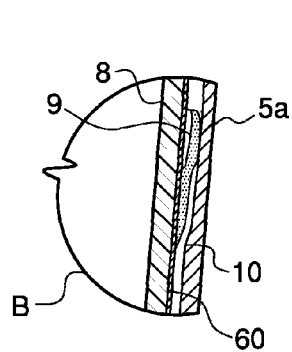
FIGS. 11-16 correspond respectively with sections B, C, D, E, F, and G of FIGS. 4, 6, 7, 8, 9 and 10.
Figure 12:
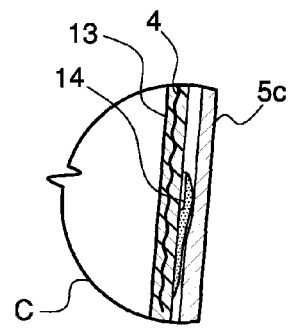

In FIG. 4, liner sleeve body portion 8 comprising an air-impermeable elastomeric material such as silicone is provided with a peripheral seal element 9 shown in more detail in FIG. 11. The seal element 9 is formed as a separate element from the liner sleeve body portion 8 and is securely attached thereto by appropriate bonding techniques that may include adhesive, heat seal, etc. In this instance, the hard socket 5a is provided with a slightly stepped portion 10 that enhances cooperation between the interior of the hard socket 5a and the seal element 9. The stepped portion 10 is not required but is optional. In this example, the seal element 9 includes a cantilevered end portion facing towards the proximal side of the liner sleeve body portion 8 to thereby enhance the ability of the seal element 9 to freely flex when a pressure differential exists on either side of the seal element 9. It will be apparent that when a higher pressure exists on the proximal side of the seal element 9 as compared with the distal side thereof, the seal element 9 will tend to expand outwardly against the interior surface of the hard socket 5a and a radial sealing force exerted by the seal will increase commensurately with the pressure differential. On the other hand, the properties of the seal and the interior wall of the hard socket 5a are such that the amputee may readily withdraw the liner sleeve body portion 8 from the hard socket 5a upon gentle pulling of the liner sleeve away from the hard socket, optionally while opening valve 7 to expose the isolated region 11 between the distal portion of the liner sleeve body portion 8 and the distal end area of the hard socket 5a to atmosphere.

Figure 5:
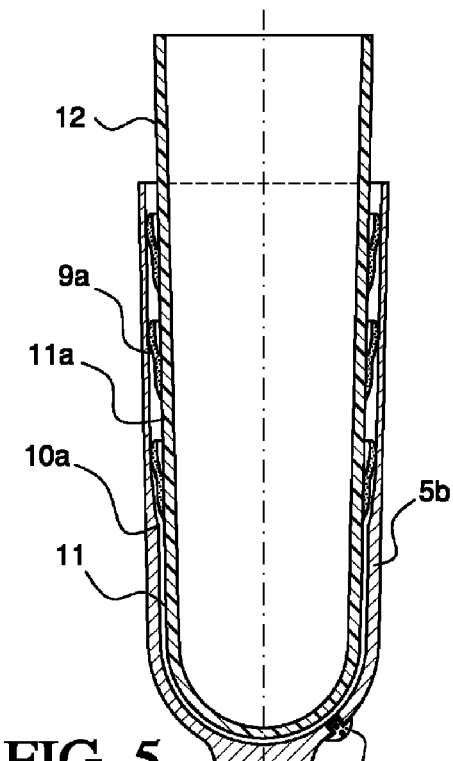

In FIG. 5, liner sleeve body portion 12 is provided with multiple, axially spaced seal elements 9a corresponding to seal element 9 in FIG. 4. This provides enhanced sealing between the liner sleeve body portion 12 and the interior of the hard socket 5b due to the multiple sealing surfaces provided and furthermore provides additional spaces 11a that are isolated from atmosphere to thereby enhance the suction effect between the liner sleeve body portion 12 and the hard socket 5b. The stepped portion 10a of the hard socket interior wall is located at a more distal region of the hard socket as compared with the stepped portion 10 in FIG. 4.

Figure 6:
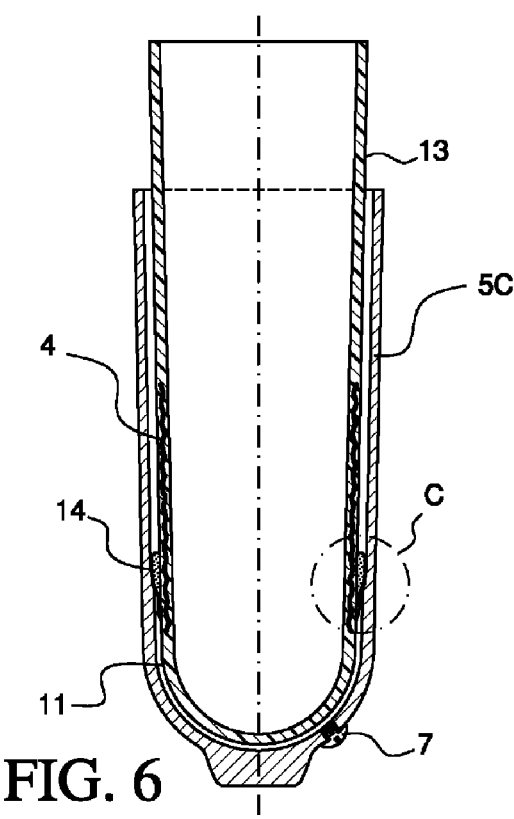

In FIG. 6, liner sleeve body portion 13 is provided with a single peripherally extending seal element 14 located towards the distal region of the liner sleeve body portion 13. The seal element 14 is formed separately from the liner sleeve body portion 13 and is secured thereto in the manner described above with respect to seal element 9 in FIG. 4. In accordance with this example, a reinforcement material 4 as described above in the example shown in FIG. 1 is provided to limit axial distension of the liner sleeve body portion 13, the reinforcement material being located in the vicinity of the seal element 14 and extending in a proximal direction relative thereto within the liner sleeve body portion 13. The seal element 14 and its relationship with the hard socket 5c in this example, the liner sleeve body portion 13 and the reinforcement material 4 are shown in more detail in FIG. 12.

Figure 7:
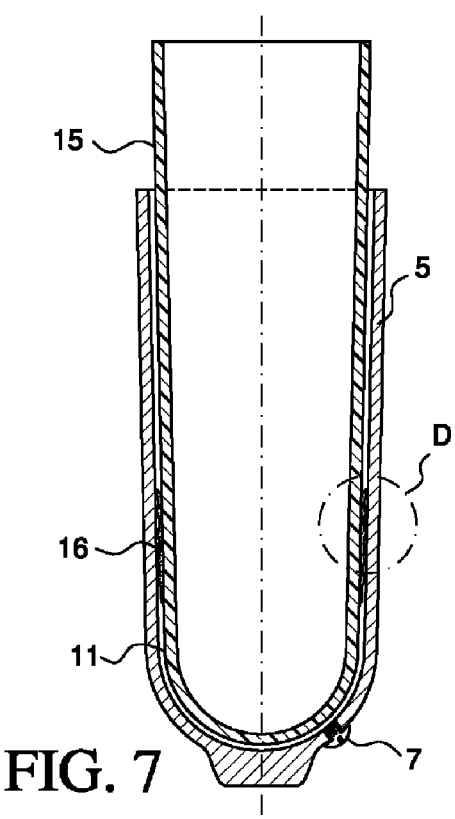
Figure 13:
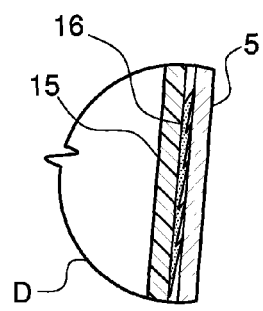
Figure 14:
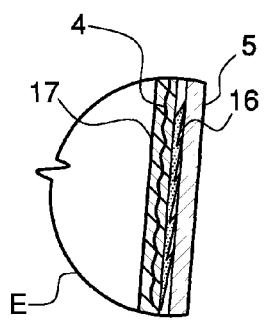

In FIG. 7, liner sleeve body portion 15 is provided with a seal assembly 16 which is shown in more detail in FIG. 13. In this example, the sleeve element 16 may be formed as a strip of material having radially bendable flaps constituting seal surfaces that, when exposed to differential pressure, will bend radially outwardly to engage the interior of the hard socket 5, which may correspond in shape to the hard socket 5 illustrated in FIG. 1. The seal element 16 may be secured to the liner sleeve body portion 15 by bonding, heat sealing, or any other appropriate bonding technique that will be readily apparent to a person skilled in the art.

Figure 8:
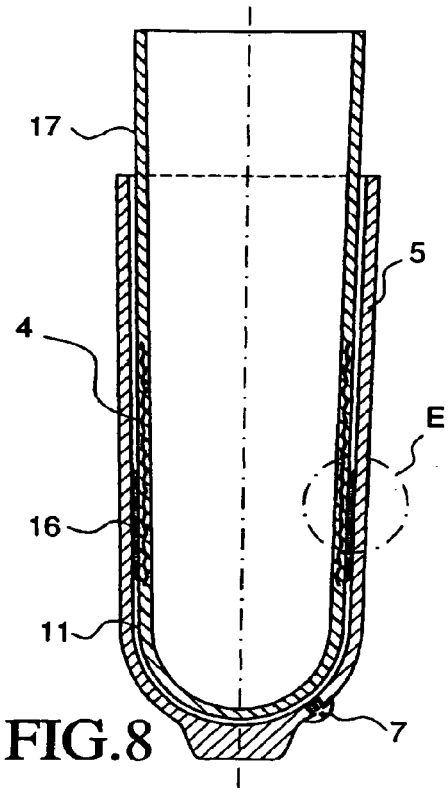

In FIG. 8, liner sleeve body portion 17 is provided with a peripheral seal element 16 which is similar to the seal element described in FIG. 13, and a reinforcement material 4 is provided in the liner sleeve body portion 17 in a manner corresponding to that described previously with regard to FIG. 6.

Figure 9:
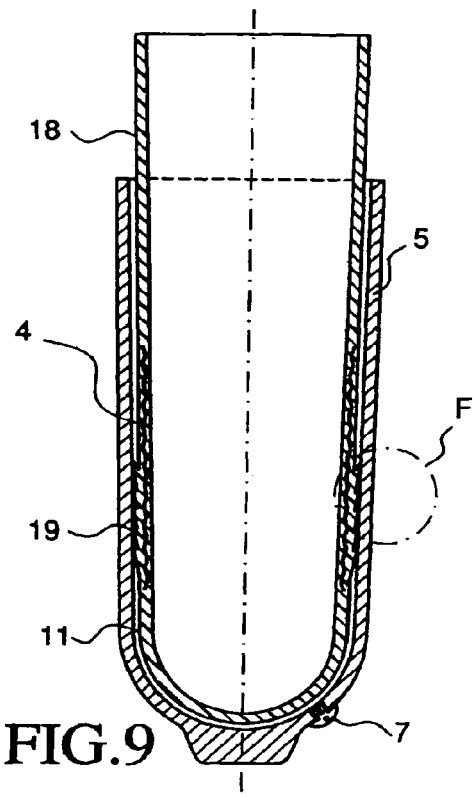
Figure 15:
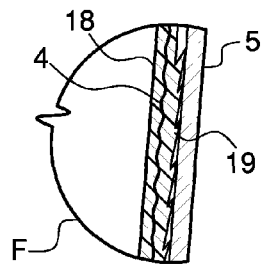
Figure 16:
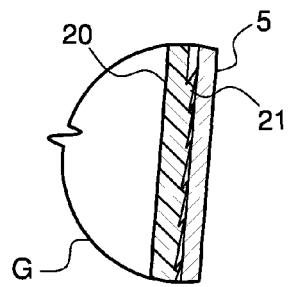

In FIG. 9, liner sleeve body portion 18 is provided with an integral peripherally extending seal element 19 that is shown in more detail in FIG. 15. The seal element 19 is integrally formed in one piece with the liner sleeve body portion 18 and comprises multiple sealing surfaces inclined radially outwardly and upwardly as shown in FIG. 15. Each radially outwardly extending element includes a sealing surface that engages the interior wall of the hard socket 5 in a manner similar to that described previously in connection with the seal elements 9, 9a, 15 and 16. That is, the form of the seal tends to increase sealing forces when the seal element is exposed to a pressure differential between the proximal and distal sides of the seal element, with the higher pressure existing towards the proximal end of the seal element. In this embodiment, a reinforcement material 4 is provided in the liner sleeve body portion 18 in the vicinity of the peripheral seal 19 and extending proximally relative thereto.

Figure 10:
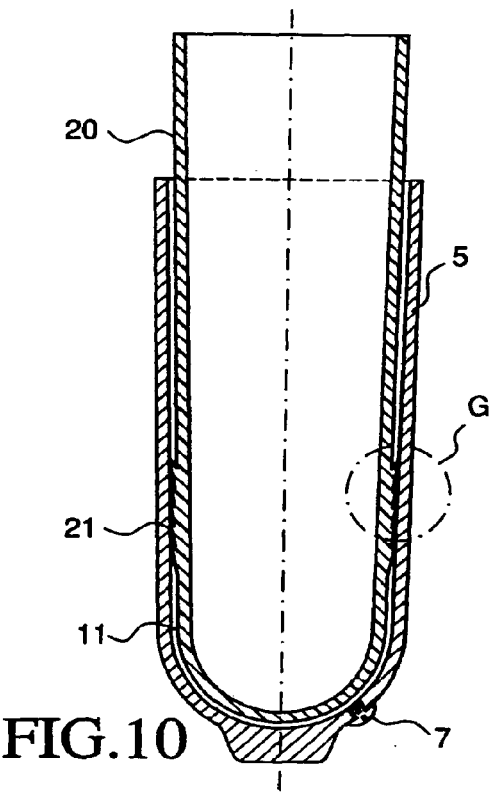

In FIG. 10, liner sleeve body portion 20 is provided with a peripheral seal 21 corresponding to seal 19 described above in connection with FIG. 9. A reinforcement material is not provided in this example. The interior of the hard socket 5 is not provided with a stepped portion in this example, although a stepped portion corresponding to the stepped portion 10 could be provided at the distal end area of the seal 21 when the liner sleeve body portion 20 is fully inserted in the hard socket 5 if desired.

With reference to FIGS. 17-20, an alternative preferred form of a liner sleeve and seal element is illustrated.

Figure 17:
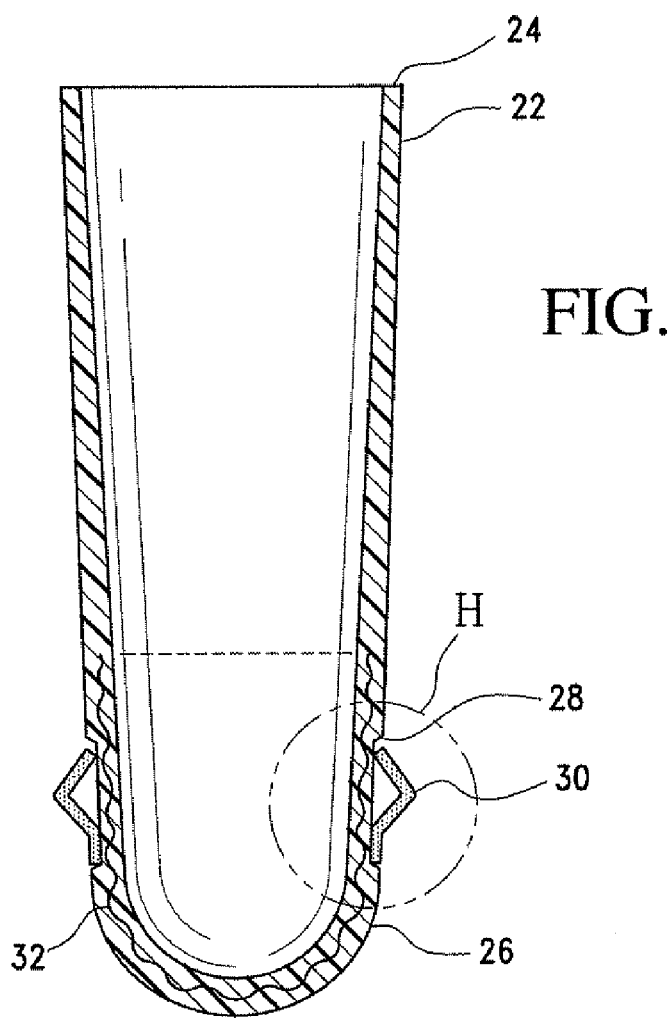
FIG. 17 is a vertical sectional view of an alternate form of an elastomer liner sleeve including a reinforcement material embedded in the liner sleeve body portion and a peripheral seal element secured to the elastomer liner sleeve in a recessed portion of the elastomer liner sleeve.

In FIG. 17, liner sleeve body portion 22 having a proximal end 24 and a distal end area 26 is provided with a recessed portion 28 and a peripheral seal element 30 radially protruding from the recessed portion 28. The recessed portion 28 extends continuously around a peripheral portion of the liner sleeve body portion 22 between the proximal and distal end areas 24, 26. The recessed portion 28 of the liner sleeve body portion 22 is configured with a length, width and depth to accommodate compression of the seal element 30. The liner sleeve body portion 22 may include a reinforcement material 32 that extends substantially around the distal area 26 of the liner sleeve body portion 22 and preferably extends at least to the seal element 30. The placement of the reinforcement material 32 is not limited to the distal end area of the liner sleeve body portion, and may extend upwardly to the proximal end 24 of the liner sleeve body portion 22.

Figure 18:
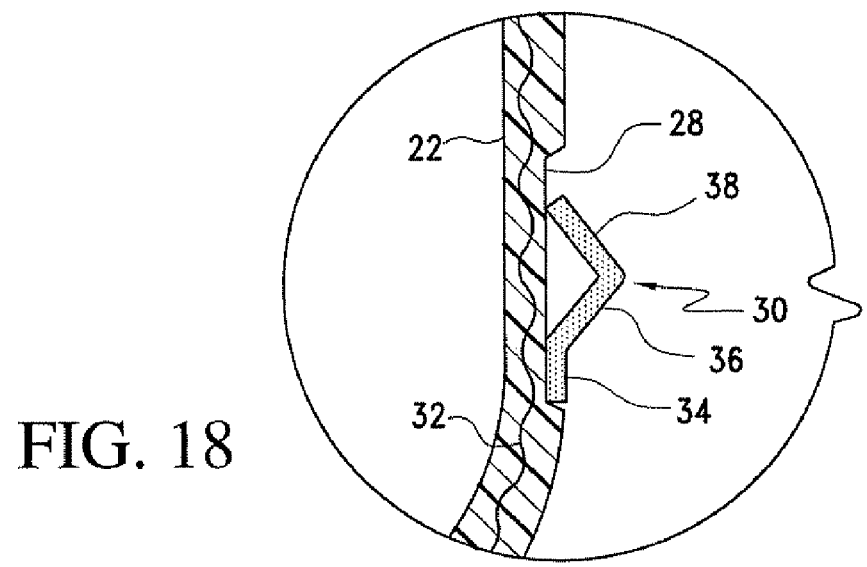
FIG. 18 corresponds to detail H in FIG. 17.

As illustrated in FIG. 18, the seal element 30 of this embodiment is formed as a separate element from the liner sleeve body portion 22, and is provided with a base member 34 that is positioned within the recessed portion 28 and is securely attached to the liner sleeve body portion 22 by appropriate bonding techniques that may include adhesive, heat seal, etc. The base member 34 is preferably parallel to the outer periphery of the liner sleeve body portion, however it will be understood that it is not limited to this orientation. The seal element 30 includes a radially outwardly pitched member 36 that extends from a
proximal end of the base member 34 and is directed towards the proximal end 24 of the liner sleeve body portion 22 at an angle relative to the base portion 32. The seal element 30 also includes a radially inwardly pitched member 38 that connects to a proximal end of the outwardly pitched member 36, and is directed towards the proximal end 24 of the liner sleeve body portion 22 at an angle relative to the base member 32.

Figure 19:
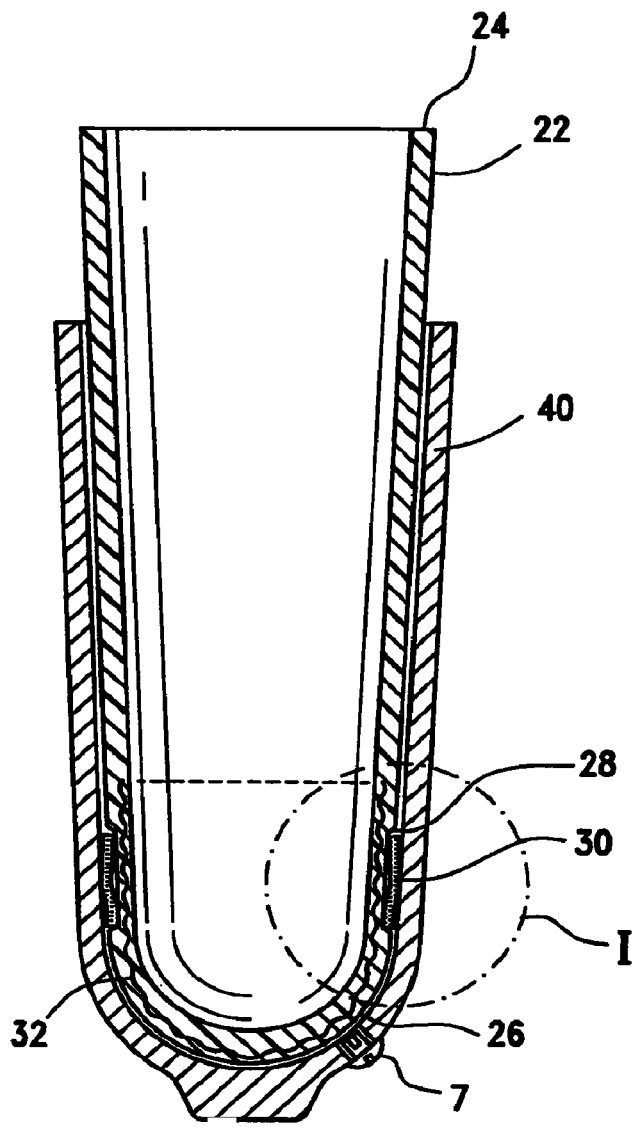
FIG. 19 is a vertical sectional view of an alternate prosthesis system including the liner sleeve of FIG. 17.

In FIG. 19, the liner sleeve body portion 22 is shown as being donned on a residual limb and the limb and liner sleeve body portion are inserted into a prosthetic hard socket 40. Preferably, the hard socket 40 includes a valve 7 located at a distal end area thereof that is of the type described above in the preceding embodiments of the present invention. When inserted in the hard socket 40, the seal element 30 is compressed so as to lie at least partially within the recessed portion 28 and bridges a seal between the liner sleeve body portion 22 and the hard socket 40. In a compressed state, the angles at which the outwardly and inwardly pitched members 36, 38 of the seal element 30 extend relative to the base member 32 are substantially less than when the liner sleeve body portion 22 is not inserted into the hard socket 40.

It will be understood that when compressed, at least a portion of the seal element should radially distend at least a distance from the recessed portion to sufficiently bridge the seal between the liner sleeve body portion and a hard socket.

Figure 20:
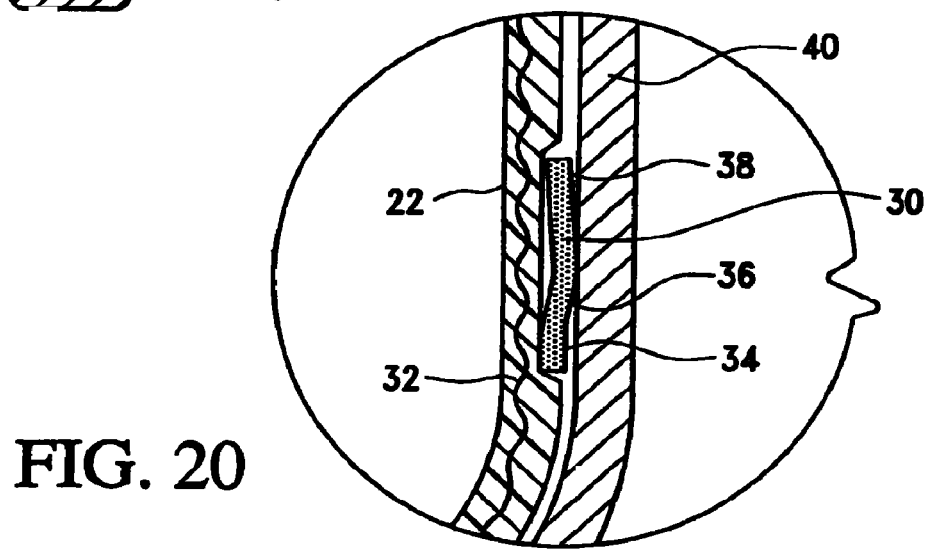
FIG. 20 corresponds to detail I in FIG. 19.

As shown in FIG. 20, the recessed portion 28 may have a depth with a dimension generally corresponding at least to the thickness of the base member 34. Moreover, the length of the recessed portion may be configured so as to have a length that is less than the combined length of the base, outwardly and inwardly members so as to prevent the seal element from becoming completely flat when the sleeve liner is inserted into a hard socket.

With reference to FIGS. 21-35, alternative preferred forms of the seal element shown in FIGS. 17-20 are illustrated. The alternative seal elements may be positioned within the recessed portion of the liner sleeve body portion or along the exterior of the liner sleeve body portion.

As shown by example in FIGS. 21-27, a seal element 42 may have radially pitched members having different lengths, thicknesses and widths, extending at different angles relative to the base member, or may be connected to one another by a connecting member 44 generally parallel with the base member. Moreover, the inwardly pitched member may include at its proximal end an extension member 46 extending generally parallel with the base portion detached from the liner sleeve body portion, or in the alternative, may extend distally beyond the connection to the outwardly pitched member. When extending beyond the outwardly pitched member, such distal portion 48 of the inwardly pitched member may have a curved, straight, or a combination of curved and straight profiles. Similarly, the outwardly pitched member may also extend proximally beyond the connection to the inwardly pitched member and such proximal portion 50 thereof may have a curved, straight, or a combination of curved and straight profiles.

In another configuration of the seal element of the invention illustrated in FIGS. 28-30, the radially outwardly and inwardly pitched members may be replaced by a curved member 52 that extends from the base member of the seal element. Said curved member may be defined as extending outwardly from the liner sleeve body portion to an apex and then extending inwardly towards the liner sleeve body portion a predetermined distance. The inwardly extending portion of the curved member may extend a distance from the apex short of the outer periphery of the liner sleeve body portion. Moreover, the curved member may include at its proximal end an extension member 54 that is detached from the liner sleeve body portion and substantially parallel with the base portion.

In yet another configuration of the seal element of the invention illustrated in FIGS. 31-35, the seal element may include a tapered segment 56 that extends proximally from the base member and under an outwardly pitched member or curved member. Furthermore, in the event the inwardly pitched member or the proximal end of the curved member is connected to an extension member 46 extending proximally therefrom, the extension member 46 may also include a tapered portion 56 distally extending under an inwardly pitched member or curved member of the seal element.

It will be understood that the aforementioned embodiments of the present invention are not limited to the described combination of the liner sleeve body portion, seal element and hard socket. Instead, the features of one of the preferred embodiments of the present invention may readily be combined with those of another or other embodiments of the present invention without departing from the scope of the present invention.

It will be readily understood that the described embodiments of the invention are exemplary only and various other features and details could be incorporated in the system described herein without departing from the spirit and scope of the invention as defined in the appended claims.

What is claimed is:

1. A suspension liner sleeve adapted to provide an interface between a residual limb and a prosthetic socket, comprising:
   an elongate, generally conical body portion having an axis and formed of a material that is at least radially extendible from a relaxed non-extended condition and defining an open proximal end and a closed distal end, an outermost layer of the body portion being formed from a textile cover;
   at least one resilient seal element formed from an elastomeric material and defining proximal and distal portions extending along the outermost layer and a middle section extending between the proximal and distal portions, the at least one seal element extending outwardly relative to the axis from the distal portion toward the proximal portion such that a thickness of the at least one seal element at the proximal portion is greater than a thickness of the at least one seal element at the distal portion, the proximal portion having a section extending substantially perpendicular relative to the axis;
   wherein the at least one seal element annularly extends around the body portion at the distal end thereof.

2. The suspension liner sleeve as claimed in claim 1, wherein a layer of the body portion is formed by an elastomeric material about which the textile cover is located.

3. The suspension liner sleeve as claimed in claim 2, wherein the at least one seal element is formed from substantially the same elastomeric material as the elastomeric layer.

4. The suspension liner sleeve as claimed in claim 2, wherein the at least one seal element is formed a softer elastomeric material than the elastomeric layer.

5. The suspension liner sleeve as claimed in claim 2, wherein the at least one seal element is formed from a stiffer elastomeric material than the elastomeric layer.

6. The suspension liner sleeve as claimed in claim 1, wherein the at least one seal element is formed as a solid mass of silicone elastomeric material.

7. A suspension liner sleeve adapted to provide an interface between a residual limb and a prosthetic socket, comprising:
   an elongate, generally conical body portion having an axis and formed of a material that is at least radially extendible from a relaxed non-extended condition and defining an open proximal end and a closed distal end, an outermost layer of the body portion being formed from a textile cover, and an elastomer layer formed by an elastomeric material covered by the textile cover;
   at least one resilient seal element having a proximal portion outwardly protruding from a distal portion relative to the axis, the distal and proximal portions secured along the outermost layer and the proximal portion arranged for deflection against the outermost layer, the at least one seal element formed from an elastomeric material;
   wherein the at least one seal element is located at a distal end of the body portion;
   wherein the elastomer layer is at least located in a vicinity of the at least one seal element wherein the outermost layer is located between elastomer layer and the at least one seal element, the elastomer layer located proximate to the at least one seal element.

8. The suspension liner sleeve as claimed in claim 7, wherein the at least one seal element is formed from substantially the same elastomeric material as the elastomer layer.

9. The suspension liner sleeve as claimed in claim 7, wherein the at least one seal element is formed a softer elastomeric material than the elastomeric material forming the elastomer layer.

10. The suspension liner sleeve as claimed in claim 7, wherein the at least one seal element is formed from a stiffer elastomeric material than the elastomeric material forming the elastomer layer.

11. The suspension liner sleeve as claimed in claim 7, wherein the at least one seal element is formed as a solid mass of silicone elastomeric material.

12. The suspension liner sleeve as claimed in claim 7, wherein the at least one seal element is formed as a ring separate from the outermost layer and secured thereon.

13. The suspension liner sleeve as claimed in claim 7, wherein the proximal portion of the at least one seal element has a section extending substantially perpendicular relative to the axis.

14. A suspension liner sleeve adapted to provide an interface between a residual limb and a prosthetic socket, comprising:
   an elongate, generally conical body portion having an axis and at least radially extendible from a relaxed non-extended condition and having an open proximal end and a closed distal end, the body portion including an outermost textile cover of the body portion and an innermost elastomeric layer opposite the outermost cover;
   at least one resilient seal element secured to the outermost cover at a distal end area thereof and formed from a solid mass of silicone material, the at least one seal element forming proximal and distal portions, the at least one seal element extending outwardly relative to the axis from the distal portion toward the proximal portion such that a thickness of the at least one seal element at the proximal portion is greater than a thickness of the at least one seal element at the distal portion;

wherein the innermost layer corresponds in location to at least the at least one seal element.

15. The suspension liner sleeve as claimed in claim 14, wherein the at least one seal element is formed from substantially the same elastomeric material as the innermost layer.

16. The suspension liner sleeve as claimed in claim 14, wherein the at least one seal element is formed a softer elastomeric material than the elastomeric material forming the innermost layer.

17. The suspension liner sleeve as claimed in claim 14, wherein the at least one seal element is formed from a stiffer elastomeric material than the elastomeric material forming the innermost layer.

18. The suspension liner sleeve as claimed in claim 14, wherein the at least one seal element is formed as a ring separate from the outermost cover and secured thereon.

19. The suspension liner sleeve as claimed in claim 14, wherein the proximal portion of the at least one seal element has a section extending substantially perpendicular relative to the axis.

* * * * *